United States Patent [19]

Strom et al.

[11] 4,149,407

[45] Apr. 17, 1979

[54] APPARATUS AND METHOD FOR CYCLIC SIMPLE SHEAR TESTING OF SOIL SAMPLES

[75] Inventors: James A. Strom, Whittier, Calif.; Roger C. H. Sidey, London, England

[73] Assignee: Dames & Moore, Los Angeles, Calif.

[21] Appl. No.: 873,224

[22] Filed: Jan. 30, 1978

[51] Int. Cl.² ............................................... G01N 3/36
[52] U.S. Cl. ......................................... 73/794; 73/815
[58] Field of Search ...................... 73/101, 91, 84, 94

[56] References Cited

U.S. PATENT DOCUMENTS

| | | | |
|---|---|---|---|
| 3,183,707 | 5/1965 | Gurney et al. | 73/101 X |
| 3,353,407 | 11/1967 | Dietert et al. | 73/101 |
| 3,494,182 | 2/1970 | Sutton | 73/84 X |

*Primary Examiner*—Jerry W. Myracle
*Attorney, Agent, or Firm*—Fulwider, Patton, Rieber, Lee & Utecht

[57] ABSTRACT

Method and apparatus for testing soil samples in which two similar samples of soil to be cyclic simple shear tested are positioned on opposite sides of a loading plate and subjected to a load normal to the plate. Simultaneously, the plate is moved transversely to apply a dynamic load to the samples. Soil response is studied by monitoring both loads and the transverse movement of the plate.

17 Claims, 2 Drawing Figures

APPARATUS AND METHOD FOR CYCLIC SIMPLE SHEAR TESTING OF SOIL SAMPLES

BACKGROUND OF THE INVENTION

The present invention relates to soil testing, and more particularly to a method and apparatus for cyclic simple shear testing.

There are many situations in which it is desired to test accurately and reliably the ability of soil samples to withstand shear producing dynamic loads. Such tests can be of crucial importance in, for example, seismic risk studies and the design of foundations for gravity-type offshore platforms and compressors. Soil responses that can be investigated in this way include cyclic deformation, compaction, liquefaction, and permanent deformation.

It is generally agreed that simple shear testing, in which uniform shear is applied over the full height of a sample, is preferable to direct shear testing, in which the shear is confined to a single plane. It should not be confused with triaxial testing in which shear is induced by compression or extension loadings. Triaxial testing has generally been conceded to be less representative of actual conditions but has been used, with correction factors applied, because triaxial equipment has been more convenient to operate or more readily available.

Cyclic simple shear testing that has been done in the recent past has involved the use of a horizontally movable carriage on which the sample to be tested is positioned. The carriage is generally mounted on wheels, but vertical legs that flex to permit horizontal movement can also be used. The sample is confined while deformation is permitted by a stack of metal rings that can slide horizontally on each other or by a wire-reinforced membrane. A piston then applies a vertical load to the top of the sample which is moved horizontally in a cyclic manner while the loads and displacement are measured electronically.

Carriage movement required by this known arrangement necessarily introduces errors, due in large measure to the friction of the carriage wheels when high vertical loads are imposed. Moreover, there is a lower limit of horizontal displacement, usually about one ten-thousandth of an inch, below which surface finish limitations prevent meaningful readings from being obtained. If flexible legs are substituted for the carriage wheels, large horizontal displacements result in distortion due to changes in the height of the sample with corresponding changes in the vertical load. Under some circumstances, a reduction in height of one thousandths of an inch can cause the vertical load to fall to zero. Other distortions present in readings conventionally obtained by cyclic simple shear testing are attributable to the inertia of the carriage which must have substantial mass if it is to withstand the loads.

It is a primary objective of the present invention to provide an improved method and apparatus for cyclic simple shear testing that is free of many of the above-mentioned disadvantages and limitations inherent in previously known techniques.

SUMMARY OF THE INVENTION

According to the present invention, soil is subjected to cyclic simple shear testing by placing similar soil samples on opposite sides of a loading plate. Each sample should be confined in such a manner that it can be deformed about an axis normal to the plate. A first load is applied to the samples by pressing them toward the loading plate, while the plate is moved transversely in a cyclic manner to apply a second load.

As the testing proceeds, the loads are applied simultaneously while both loads and the transverse plate displacement are monitored, preferably using a conventional arrangement of transducers for this purpose. It should be noted that no carriage or equivalent travel-permitting mechanism is required to accommodate the desired loading plate movement and deformation of the samples. Both samples remain fixed at their outer ends and their inner ends move with the loading plate as sample deformation takes place.

To apply the first load, the samples and loading plate can be positioned between a piston and a stationary member. In a preferred arrangement, the samples are confined and positioned with respect to the loading plate by stacks of rings, each ring being free to slide on the others to permit deformation of the samples.

Other features and advantages of both the apparatus and method of the present invention will become apparent from the following detailed description, taken in conjunction with the accompanying drawings, which illustrate, by way of example, principles of the invention.

DESCRIPTION OF THE PREFERRED EMBODIMENT

Figure 1:
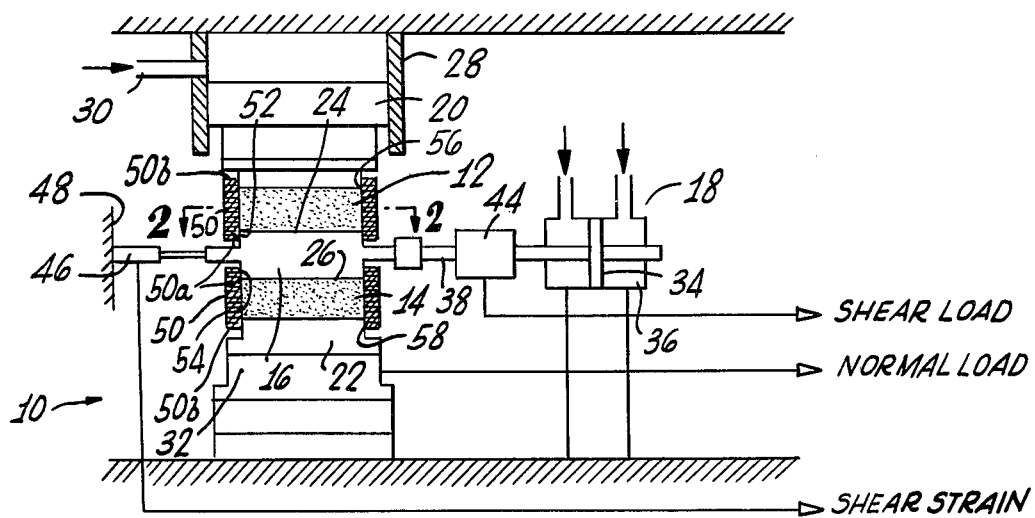
FIG. 1 is a schematic illustration of apparatus constructed in accordance with the invention, for cyclic simple shear testing of soil samples, portions of the apparatus being shown in section.

An apparatus 10 that embodies many aspects of the present invention, illustrated in FIG. 1 of the accompaying drawings, utilizes two similar samples 12 and 14 of the soil to be subjected to cyclic simple shear testing. In general, it comprises a loading plate 16 located between the samples 12 and 14, an actuator 18 for applying a dynamic load to the sample, a piston 20, and a stationary member 22 that opposes the piston so that a static normal load can be applied to the samples.

Figure 2:
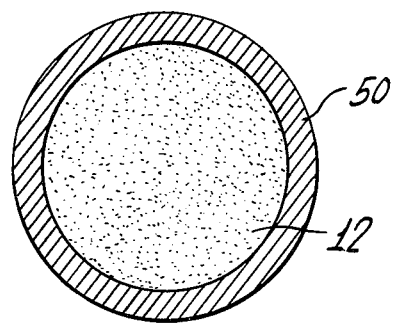
FIG. 2 is an enlarged cross-sectional view taken horizontally through one of the soil samples and its confining structure, taken along the line 2—2 of FIG. 1.

The loading plate 16 is generally disk-shaped with its flat loading surfaces 24 and 26 oriented horizontally. The samples 12 and 14 are also disk-shaped, as shown in FIG. 2, and are located on opposite sides of the loading plate 16, bearing against its flat surfaces 24 and 26.

Supporting the lower sample 14 is the stationary member 22 which has a horizontal top surface, so that the sample is positioned vertically between the stationary member and the lower loading plate surface 26. The upper sample 12 is held between the horizontal bottom surface of the piston 20 and the top 24 of the loading plate 16. The piston 20 is slidably received for vertical movement within a pneumatic cylinder 28. When air is admitted to the cylinder 28, through an inlet 30, the piston 20 is urged downwardly toward the stationary member 22 and both samples 12 and 14 are pressed against the loading plate 16. In this manner, a vertical static load, normal to the loading plate 16, is applied to the samples 12 and 14. A transducer 32 attached to the stationary member 22 senses the magnitude of this static load.

The actuator 18, in this exemplary embodiment, includes a double acting piston 34 movable horizontally within a cylinder 36 and connected to the loading plate 16 by a rod 38. The piston 34 reciprocates within the cylinder 36 as fluid is admitted through inlets 40 and 42 on opposite sides. The fluid flow can be controlled by a conventional flapper valve (not shown).

Reciprocation of the actuator piston 34 causes transverse cyclical movement of the loading plate 16 in a horizontal plane normal to the direction of the static load. The magnitude of this dynamic load, or shear load, is sensed by a transducer 44 positioned between piston 34 and the rod 38. Transverse movement of the loading plate 16 in response to the dynamic load, i.e., shear strain, is sensed by a transducer 46 disposed between a fixed support 48 and the loading plate 16 on the opposite side of the plate from the actuator 18.

During the test, the samples 12 and 14 are positioned adjacent the top and bottom surfaces 24 and 26 of the loading plate 16 but are each permitted to deform about a vertical axis normal to the loading plate as the plate moves transversely. The surfaces 24 and 26 of the loading plate, the stationary member 22 and the piston 20 that contact the ends of the samples 12 and 14 are roughened so that the sample is frictionally held against free transverse movement during testing.

Each sample 12, 14 is confined within a stack of Teflon coated steel rings 50. As the loading plate 16 moves transversely, the rings 50 slide on each other to permit deformation of the samples 12 and 14. At the inner ends of the samples 12 and 14, the rings 50a closest to the loading plate 16 are positioned by short annular walls 52 and 54 that surround the upper and lower loading plate surfaces 24 and 26. The rings 50b at the outer ends of the stacks are positioned by similar annular walls 56 and 58 carried by the piston 20 and the stationary member 22, respectively. The rings 50a and 50b interlock loosely with the annular walls 52, 54, 56 and 58, permitting sufficient transverse movement that the samples 12 and 14 are held during testing by friction alone.

It will be apparent that the readings obtained by monitoring the outputs of the transducers 32, 44 and 46 give an indication of soil response that is substantially uneffected by the characteristics of any carriage or other moving part supporting the samples, all transverse movement of the loading plate 16 being permitted by the deformation of the samples 12 and 14 themselves. The transducer outputs may be recorded graphically or displayed as digital readouts, as desired. Considerations of surface finish do not prevent testing at low horizontal displacement levels. In fact, a low displacement, high frequency, electro-magnetic actuator can be substituted for the hydraulic actuator 18 described above. There is no variation in the distance across which the static load is applied, even at high displacement levels. The apparatus 10 is also simple, reliable and convenient to use.

While a particular form of the invention has been illustrated and described, it will also be apparent that various modifications can be made without departing from the spirit and scope of the invention.

We claim:

1. An apparatus for cyclic simple shear testing of soil samples comprising:
   a loading plate;
   dynamic loading means for imparting transverse cyclic movement to said loading plate;
   confining means for confining and positioning samples on opposite sides of said loading plate while permitting deformation of said samples along an axis normal to said loading plate, said confining means comprising a stack of rings slidable on each other; and
   normal loading means for applying a normal load to said samples in the direction of said loading plate and thereby pressing said samples against said loading plate.

2. The apparatus of claim 1 wherein said normal load is a static load.

3. An apparatus for cyclic simple shear testing of soil samples comprising:
   a loading plate having first and second loading surfaces;
   two stacks of rings slidable on each other and disposed adjacent said loading surfaces to position and confine soil samples while permitting deformation of said samples along an axis normal to said loading plate;
   a stationary member spaced from said first loading surface to permit one of said stacks of rings and a corresponding soil sample to be positioned between said stationary member and said first loading surface;
   a piston spaced from said second loading surface to permit another of said stacks of rings and a corresponding soil sample to be positioned between said piston and said second loading surface;
   means for urging said piston toward said stationary member to apply a static load to said soil samples;
   dynamic loading means for imparting a transverse cyclic movement to said loading plate in a plane normal to said static load;
   first transducer means for measuring the displacement of said loading plate produced by said dynamic loading means;
   second transducer means for measuring the load applied to said soil samples by said dynamic loading means; and
   third transducer means for measuring the static load applied to said samples by said piston.

4. A method for cyclic simple shear testing of soil samples comprising:
   obtaining two similar samples of the soil to be tested;
   placing said samples on opposite sides of a loading plate;
   applying a first load to said samples and thereby pressing said samples against said loading plate; and
   applying a dynamic second load to said samples by moving said loading plate cyclically in a transverse plane normal to said first load.

5. The method of claim 4 further comprising monitoring said second load, dynamic load and transverse displacement applied to said samples.

6. The method of claim 4 further comprising positioning and confining said samples with respect to said plate while permitting deformation thereof along an axis normal to said transverse movement.

7. The method of claim 4 further comprising positioning and confining said samples with respect to said plate by placing each of said samples within a stack of rings that are free to slide on each other, thereby permitting deformation of said samples along an axis normal to said transverse movement.

8. The method of claim 4 wherein said second load is applied to said samples by:
   positioning one of said samples between said loading plate and a stationary member;

positioning the other of said samples between said loading plate and a piston; and urging said piston toward said stationary member.

9. The method of claim 4 wherein said first load is a static load.

10. A method for cyclic simple shear testing of soil samples comprising:
   obtaining two similar samples of the soil to be tested;
   placing one of said samples between a stationary member and a loading plate;
   placing the other of said samples between a piston and the opposite side of said loading plate;
   confining each of said samples within a stack of rings that are movable on each other to permit distortion of said samples along axes normal to said loading plate;
   urging said piston toward said stationary member and thereby applying a static load to said samples;
   cyclically moving said plate transversely in a plane normal to said static load and thereby applying a dynamic load to said samples; and
   monitoring the static load, dynamic load and transverse displacement applied to said sample.

11. An apparatus for cyclic simple shear testing of soil samples comprising:
   a loading plate;
   dynamic loading means for imparting transverse cyclic movement to said loading plate;
   means for confining and positioning samples on opposite sides of said loading plate; and
   normal loading means for applying a normal load to said samples in the direction of said loading plate and thereby pressing said samples against said loading plate, said normal loading means comprising a stationary member on one side of said loading plate and a piston on the opposite side of said loading plate, said piston being movable toward said stationary member.

12. The apparatus of claim 11 wherein said normal load is a static load.

13. An apparatus for cyclic simple shear testing of soil samples comprising:
   a loading plate;
   dynamic loading means for imparting transverse cyclic movement to said loading plate;
   means for confining and positioning samples on opposite sides of said loading plate;
   normal loading means for applying a normal load to said samples in the direction of said loading plate and thereby pressing said samples against said loading plate; and
   sensor means for measuring the cyclic load applied to said samples.

14. The apparatus of claim 13 wherein said normal load is a static load.

15. An apparatus for cyclic simple shear testing of soil samples comprising:
   a loading plate;
   dynamic loading means for imparting transverse cyclic movement to said loading plate;
   means for confining and positioning samples on opposite sides of said loading plate;
   normal loading means for applying a normal load to said samples in the direction of said loading plate and thereby pressing said samples against said loading plate; and
   sensor means for measuring the normal load applied to said samples.

16. The apparatus of claim 15 further comprising sensor means for measuring the displacement of said loading plate produced by said dynamic loading means.

17. The apparatus of claim 15 wherein said normal load is a static load.

* * * * *